US010166122B2

(12) United States Patent  
Park et al.

(10) Patent No.: US 10,166,122 B2  
(45) Date of Patent: Jan. 1, 2019

(54) APPARATUS FOR CONTROLLING PROSTHETIC ARM

(71) Applicant: Korea Institute of Science and Technology, Seoul (KR)

(72) Inventors: Sung Kee Park, Seoul (KR); Dong Hwan Kim, Seoul (KR); Hui Je Che, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 164 days.

(21) Appl. No.: 14/654,115

(22) PCT Filed: Dec. 19, 2013

(86) PCT No.: PCT/KR2013/011864  
§ 371 (c)(1),  
(2) Date: Jun. 19, 2015

(87) PCT Pub. No.: WO2014/098494  
PCT Pub. Date: Jun. 26, 2014

(65) Prior Publication Data  
US 2015/0328019 A1    Nov. 19, 2015

(30) Foreign Application Priority Data

Dec. 20, 2012    (KR) ........................ 10-2012-0149328

(51) Int. Cl.  
*A61F 2/70* (2006.01)  
*A61F 2/54* (2006.01)  
(Continued)

(52) U.S. Cl.  
CPC ............... *A61F 2/70* (2013.01); *A61F 2/54* (2013.01); *A61F 2/583* (2013.01); *A61F 2/68* (2013.01);  
(Continued)

(58) Field of Classification Search  
CPC ............... A61F 2/70; A61F 2/54; A61F 2/68  
See application file for complete search history.

(56) References Cited

U.S. PATENT DOCUMENTS

2006/0061544 A1\* 3/2006 Min .................. G02B 27/0093  
345/156  
2006/0167564 A1\* 7/2006 Flaherty ............... A61B 5/0476  
623/57

(Continued)

FOREIGN PATENT DOCUMENTS

JP    2004-254876 A    9/2004  
JP    2010-051682 A    3/2010  
(Continued)

OTHER PUBLICATIONS

International Search Report dated Apr. 28, 2014 in counterpart International Application No. PCT/KR2013/011864 (4 pages, with English translation).

*Primary Examiner* — Shaheda Abdin  
(74) *Attorney, Agent, or Firm* — NSIP Law

(57) ABSTRACT

The present invention provides an apparatus for controlling an artificial hand, including: a head-up display interface portion; and a controller which controls the artificial hand in accordance with an input of the head-up display interface portion, the head-up display interface portion receiving the input based on movement of a user's eyes or pupil.

14 Claims, 6 Drawing Sheets

(51) Int. Cl.
  *A61F 2/58* (2006.01)
  *A61F 2/72* (2006.01)
  *A61F 2/68* (2006.01)

(52) U.S. Cl.
  CPC ........ *A61F 2/72* (2013.01); *A61F 2002/6881* (2013.01); *A61F 2002/701* (2013.01); *A61F 2002/704* (2013.01); *A61F 2002/705* (2013.01)

(56) References Cited

U.S. PATENT DOCUMENTS

| | | | |
|---|---|---|---|
| 2008/0208396 A1* | 8/2008 | Cairola | G06F 3/011 701/3 |
| 2009/0088774 A1* | 4/2009 | Swarup | A61B 34/37 606/130 |
| 2011/0077471 A1* | 3/2011 | King | A61B 5/16 600/300 |
| 2012/0194419 A1* | 8/2012 | Osterhout | G02B 27/0093 345/156 |

FOREIGN PATENT DOCUMENTS

| | | |
|---|---|---|
| JP | 2012-050837 A | 3/2012 |
| KR | 10-2008-0077804 A | 8/2008 |

* cited by examiner

Fig. 9

| Power | | | Precision |
|---|---|---|---|
| Prismatic | Hook (+Lateral Pinch) | Circular | Circular |

APPARATUS FOR CONTROLLING PROSTHETIC ARM

CROSS-REFERENCE TO RELATED APPLICATION

This application claims priority to and the benefit of Korean Patent Application No. 10-2012-0149328 filed in the Korean Intellectual Property Office on Dec. 20, 2012, the entire contents of which are incorporated herein by reference.

BACKGROUND OF THE INVENTION (a) Field of the Invention

The present invention relates to an apparatus for controlling an artificial hand, and more particularly to an apparatus for controlling an artificial hand, which is more convenient for an actual user who controls the artificial hand, solves a problem of signal degradation of an electromyogram caused by muscular fatigue or sweat due to long-time use, and materializes his/her various commands.

(b) Description of the Related Art

As a conventional method of controlling an artificial hand, technology of using electromyogram (EMG) has been researched and developed.

However, the method based on such researches and developments has had a problem of limiting the number of inputs applied using the electromyogram to four (e.g., a commercialized product has a limit of allowing about four kinds of input). Thus, it has been difficult to materialize a user's various commands (orders, instructions) for controlling an artificial hand.

Further, long-time wear of a control apparatus has caused signal degradation of the electromyogram due to a user's fatigue or sweat.

In addition, a user who wants to control an artificial hand has to be requisitely trained for controlling the electromyogram, and thus there are many difficulties in substantive use.

Under such circumstances, there has been continuously required an apparatus for controlling an artificial hand, which is more convenient for an actual user who wants to control the artificial hand, solves a problem of signal degradation of an electromyogram caused by muscular fatigue or sweat due to long-time use, and materializes his/her various commands.

RELATED REFERENCE

Patent Document

Korean Patent Publication No. 2011-0068710 (Jun. 22, 2011), entitled "GRIPPING CONTROL DEVICE FOR ARTIFICIAL ARM"

SUMMARY OF THE INVENTION

Accordingly, the present invention is conceived to solve the forgoing problems, and an aspect of the present invention is to provide an apparatus for controlling an artificial hand, which is more convenient for an actual user who wants to control the artificial hand, solves a problem of signal degradation of an electromyogram caused by muscular fatigue or sweat due to long-time use, and materializes his/her various commands.

In accordance with an aspect of the present invention, there is provided an apparatus for controlling an artificial hand, including: a head-up display interface portion; and a controller which controls the artificial hand in accordance with an input of the head-up display interface portion, the head-up display interface portion receiving the input based on movement of a user's eyes or pupil.

The head-up display interface portion may be provided to be worn on a face.

The head-up display interface portion to be worn on may include a pair of glasses or a pair of sunglasses.

The apparatus for controlling an artificial hand may further include an electromyogram input portion for measuring a user's electromyogram, wherein the controller controls the artificial hand in accordance with an input in the electromyogram input portion in addition to the input in the head-up display interface portion.

The head-up display interface portion may include a camera provided at one side thereof to receive an input by tracking movement of a user's eye or pupil.

The head-up display interface portion may include a basic-mode portion, a gesture-mode portion, and a grip-mode portion.

The basic-mode portion may be configured to select at least one among a menu for entering the gesture-mode portion, a menu for entering the grip-mode portion, a menu for bending or stretching an elbow, and a stop menu for stopping operations of the artificial hand.

The gesture-mode portion may be configured to select at least one among a previous menu for returning to a previous stage, a menu for returning back to the basic-mode portion, a menu for bending or stretching an elbow, a stop menu for stopping operations of the artificial hand, an indexing menu for spreading out only an index finger while closing a hand, and a thumb-up menu for spreading out only a thumb while closing a hand.

The grip-mode portion may include a grip-type selection portion, a wrist-rotation selection portion and an open/close selection portion.

The grip-type selection portion may be configured to select at least one among a previous menu for returning to a previous stage, a menu for returning to the basic-mode portion, a menu for bending or stretching an elbow, a stop menu for stopping operations of the artificial hand, a prismatic menu for a general grip, a hook menu for a grip while sticking out a thumb, a power circular menu for outstretching fingers to grip a circular object, a precision circular menu for adjusting fingers to a small and circular object, a next menu for entering a next stage.

The wrist-rotation selection portion may be configured to select at least one among a previous menu for returning to a previous stage, a menu for returning back to the basic-mode portion, a menu for bending or stretching an elbow, a stop menu for stopping operations of the artificial hand, a clockwise wrist-rotation menu for rotating a wrist in a clockwise direction, a counterclockwise wrist-rotation menu for rotating a wrist in a counterclockwise direction, and a menu for entering a next stage.

The open/close selection portion may be configured to select at least one among a previous menu for returning to a previous stage, a menu for returning back to the basic-mode portion, a menu for bending or stretching an elbow, a stop menu for stopping operations of the artificial hand, a hand-open menu for opening a hand, and a hand-close menu for closing the hand.

The apparatus for controlling an artificial hand may further include an electromyogram input portion for measuring a user's electromyogram, wherein the controller controls the artificial hand in accordance with an input in the electromyogram input portion in addition to the input in the head-up display interface portion.

The selection of the menu in the head-up display interface portion may be replaced, paralleled or complemented by the input in the electromyogram input portion.

The apparatus for controlling an artificial hand may further include a blink detector for detecting a user's blink, wherein the controller controls the artificial band in accordance with an output of the blink detector in addition to the input in the head-up display interface portion.

The selection of the menu in the head-up display interface portion may be replaced, paralleled or complemented by the output from the blink detector.

The stop menu for stopping the operations of the artificial hand may be selected by blinking a user's eyes twice.

BRIEF DESCRIPTION OF THE DRAWINGS

The above and/or other aspects of the present invention will become apparent and more readily appreciated from the following description of the exemplary embodiments, taken in conjunction with the accompanying drawings, in which:

FIG. 9 is a view for explaining grip types.

DETAILED DESCRIPTION OF THE EMBODIMENTS

Figure 1:
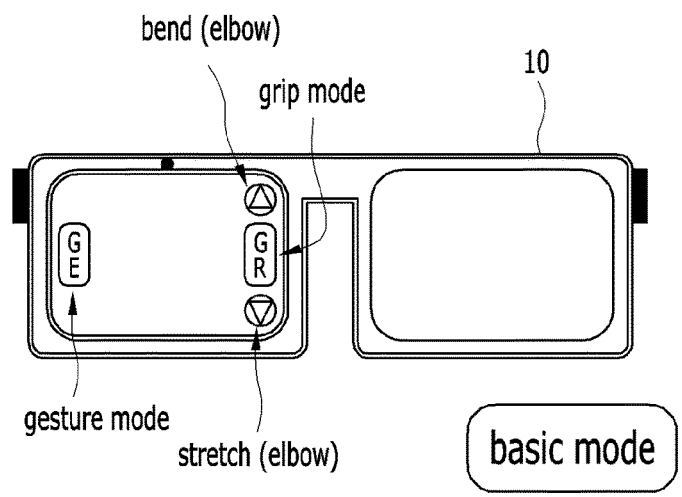
FIG. 1 is a view showing a basic-mode portion in an apparatus for controlling an artificial hand according to an embodiment of the present invention.

Hereinafter, exemplary embodiments according to the present invention will be described with reference to accompanying drawings. Also, terms and words used in the following description and claims have to be interpreted by not the limited meaning of the typical or dictionary definition, but the meaning and concept corresponding to the technical idea of the present invention on the assumption that the inventor can properly define the concept of the terms in order to describe his/her own invention in the best way.

Further, embodiments described in this specification and elements shown in the drawings are nothing but preferable examples, and do not represent the entirety of the present technical idea. Accordingly, it will be appreciated that they may be replaced by various equivalents and modifications on the filing date of the present invention.

Figure 2:
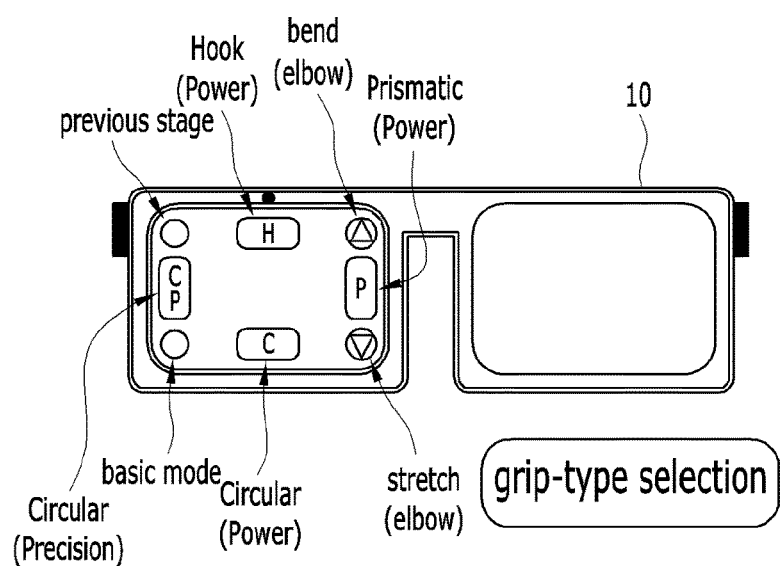
FIG. 2 is a view showing a grip-type selection portion in an apparatus for controlling an artificial hand according to an embodiment of the present invention.
Figure 3:
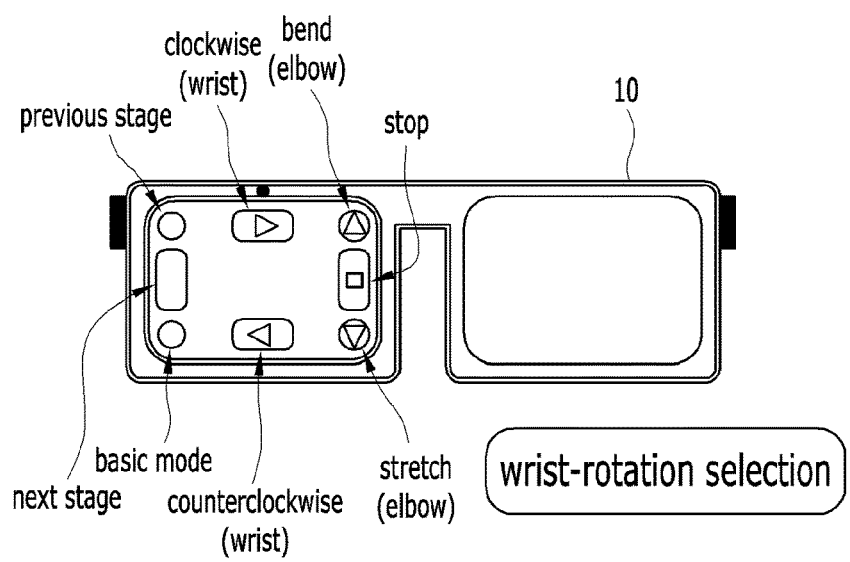
FIG. 3 is a view showing a wrist-rotation selection portion in an apparatus for controlling an artificial hand according to an embodiment of the present invention.
Figure 4:
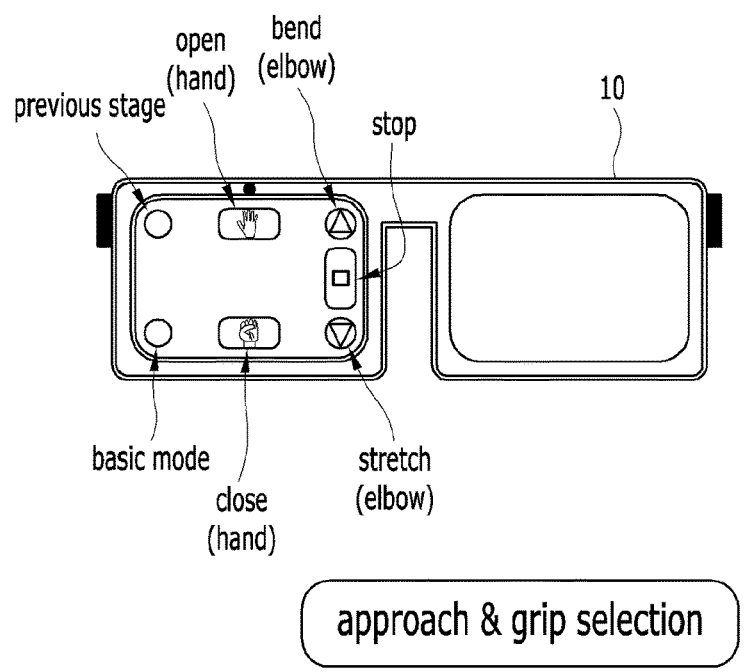
FIG. 4 is a view showing an open/close selection portion in an apparatus for controlling an artificial hand according to an embodiment of the present invention.
Figure 5:
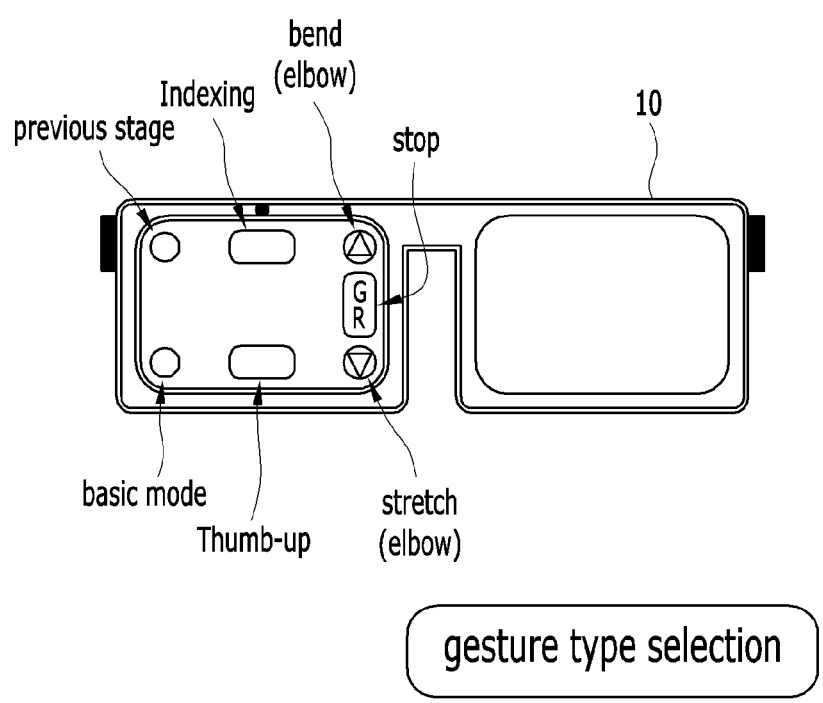
FIG. 5 is a view showing a gesture-mode portion in an apparatus for controlling an artificial hand according to an embodiment of the present invention.
Figure 6:
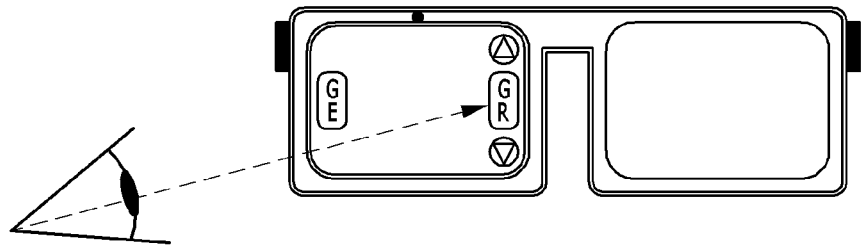
FIG. 6 is a view schematically showing an input based on eye tracking in a head-up display interface portion according to an embodiment of the present invention.
Figure 7:
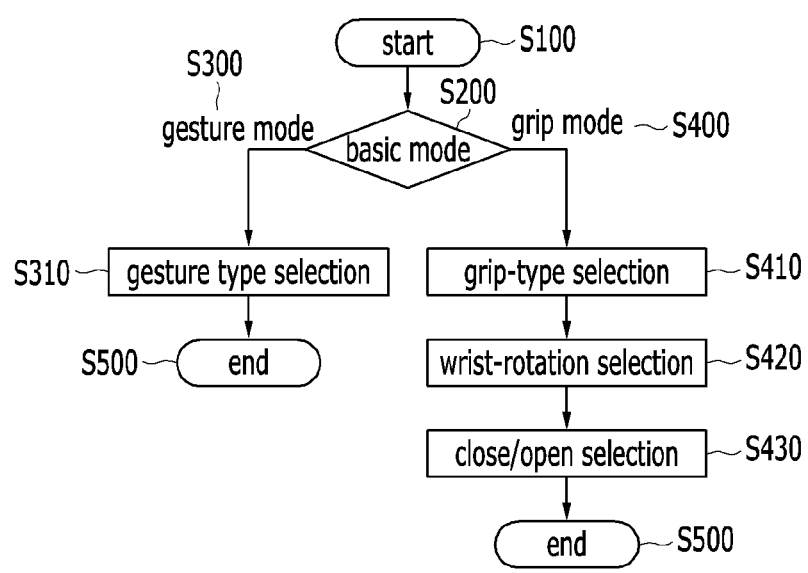
FIG. 7 is a flowchart showing operations of an apparatus for controlling an artificial hand according to an embodiment of the present invention.
Figure 8:
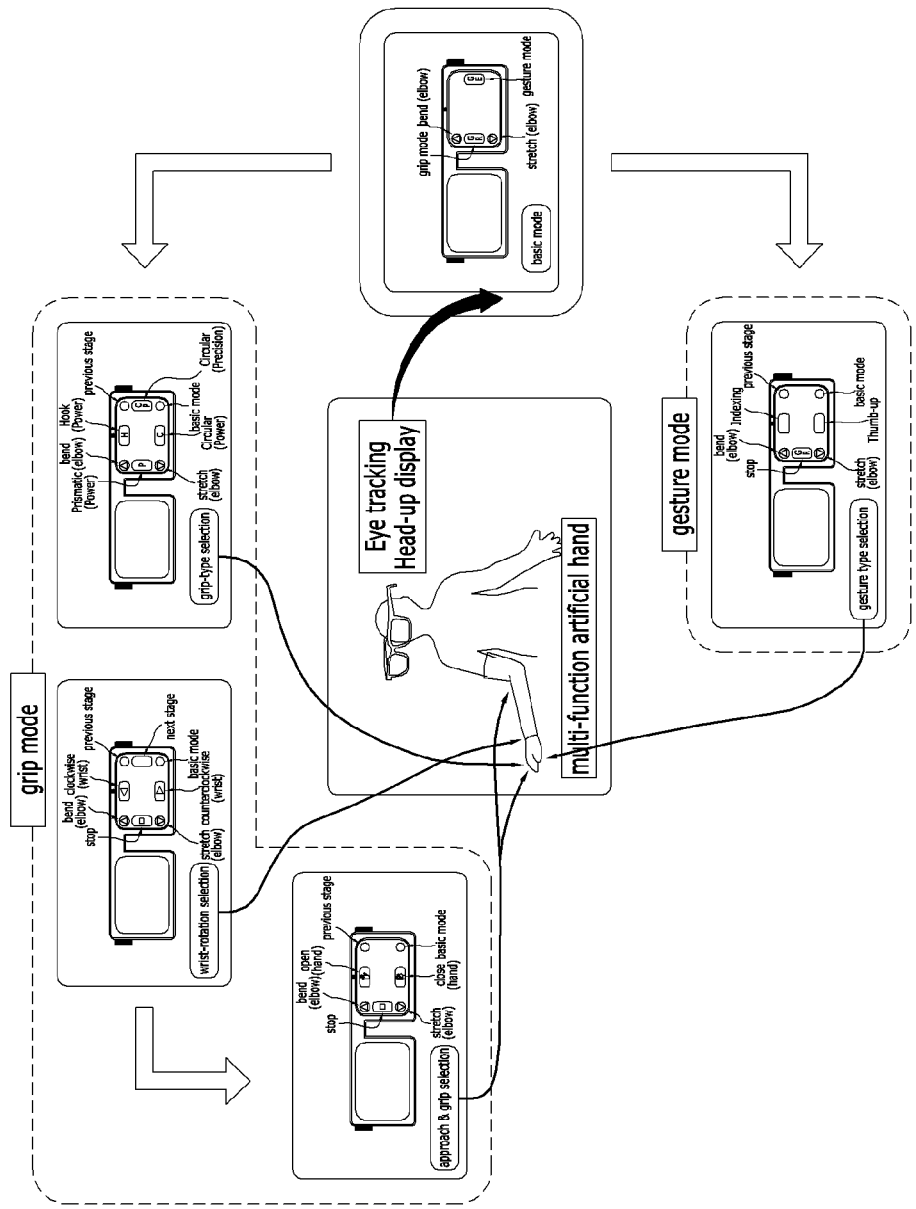
FIG. 8 is a view showing a whole control method of an apparatus for controlling an artificial hand according to an embodiment of the present invention.

FIG. 1 is a view showing a basic-mode portion in an apparatus for controlling an artificial hand according to an embodiment of the present invention, FIG. 2 is a view showing a grip-type selection portion in an apparatus for controlling an artificial hand according to an embodiment of the present invention, FIG. 3 is a view showing a wrist-rotation selection portion in an apparatus for controlling an artificial hand according to an embodiment of the present invention, FIG. 4 is a view showing an open/close selection portion in an apparatus for controlling an artificial hand according to an embodiment of the present invention, FIG. 5 is a view showing a gesture-mode portion in an apparatus for controlling an artificial hand according to an embodiment of the present invention, FIG. 6 is a view schematically showing an input based on eye tracking in a head-up display interface portion according to an embodiment of the present invention, FIG. 7 is a flowchart showing operations of an apparatus for controlling an artificial hand according to an embodiment of the present invention, FIG. 8 is a view showing a whole control method of an apparatus for controlling an artificial hand according to an embodiment of the present invention, and FIG. 9 is a view for explaining grip types.

As shown therein, an apparatus for controlling an artificial hand according to an embodiment of the present invention includes a head-up display interface portion 10; and a controller for controlling an artificial hand (not shown) in accordance with an input of the head-up display interface portion, in which the head-up display interface portion 10 receives the input based movement of on a user's eyes or pupil.

The head-up display interface portion 10 is provided to be worn on a user's face. Typically, the head-up display interface portion 10 is generally provided in the form of a pair of glasses or sunglasses to be worn on the face, but not limited thereto. Alternatively, the head-up display interface portion 10 may be provided in the form of a helmet or the like.

Connection between the head-up display interface portion 10 and the controller, and connection between the controller and the artificial hand may be achieved not only by a wire but also wirelessly. The wireless connection may employ various publicly known communication standards.

As shown in FIG. 6, the head-up display interface portion 10 (glasses, sunglasses, a helmet, etc.) is provided with a camera at one side thereof to receive an input by tracking movement of a user's eye or pupil.

As shown in FIGS. 1 to 8, the head-up display interface portion 10 includes a basic-mode portion, a gesture-mode portion, and a grip-mode portion.

As shown in FIG. 1, the basic-mode portion may be configured to select at least one among a menu for entering the gesture-mode portion, a menu for entering the grip-mode portion, a menu for bending or stretching an elbow, and a stop menu for stopping operations of the artificial hand.

As shown in FIGS. 2 to 4, the grip-mode portion includes a grip-type selection portion, a wrist-rotation selection portion and an open/close open/close selection portion.

As shown in FIG. 2, the grip-type selection portion may be configured to select at least one among a previous menu for returning to a previous stage, a menu for returning to the basic-mode portion, a menu for bending or stretching an elbow, a stop menu for stopping operations of the artificial hand, a prismatic menu for a general grip, a hook menu for a grip while sticking out a thumb, a power circular menu for outstretching fingers to grip a circular object, a precision circular menu for adjusting fingers to a small and circular object, a next menu for entering a next stage.

In this regard, FIG. 9 illustrates grip-types. The prismatic menu, the hook menu, and the power circular menu are power menus on the contrary to the precision menu. Of course, the sort and classification of the menus may be changed, altered or modified by a designer of the apparatus for controlling the artificial hand.

As shown in FIG. 3, the wrist-rotation selection portion may be configured to select at least one among a previous menu for returning to a previous stage, a menu for returning back to the basic-mode portion, a menu for bending or stretching an elbow, a stop menu for stopping operations of the artificial hand, a clockwise wrist-rotation menu for rotating a wrist in a clockwise direction, a counterclockwise wrist-rotation menu for rotating a wrist in a counterclockwise direction, and a menu for entering a next stage.

As shown in FIG. 4, the open/close selection portion may be configured to select at least one among a previous menu for returning to a previous stage, a menu for returning back to the basic-mode portion, a menu for bending or stretching an elbow, a stop menu for stopping operations of the artificial hand, a hand-open menu for opening a hand, and a hand-close menu for closing the hand.

As shown in FIG. 5, the gesture-mode portion may be configured to select at least one among a previous menu for returning to a previous stage, a menu for returning back to the basic-mode portion, a menu for bending or stretching an elbow, a stop menu for stopping operations of the artificial hand, an indexing menu for spreading out only an index finger while closing a hand, and a thumb-up menu for spreading out only a thumb while closing a hand.

In addition, a blink detector may be provided for detecting a user's blink. The controller may control the artificial hand in accordance with an output of the blink detector in addition to the input in the head-up display interface portion.

Further, the selection of the menu in the head-up display interface portion may be replaced, paralleled or complemented by the output of the blink detector. For example, the stop menu for stopping the operations of the artificial hand may be set to be selected by blinking a user's eyes twice.

Such settings may be changed by a user freely through the controller (not shown) with regard to the most frequently used items.

Alternatively, the apparatus for controlling an artificial hand may further include an electromyogram input portion for measuring a user's electromyogram. The controller may control the artificial hand in accordance with an input in the electromyogram input portion in addition to the input in the head-up display interface portion. The selection of the menu in the head-up display interface portion may be replaced, paralleled or complemented by the input in the electromyogram input portion.

The foregoing menus are just given for explaining the present invention, and may be properly changed by a designer of the apparatus for controlling the artificial hand.

FIG. 7 is a flowchart showing operations of an apparatus for controlling an artificial hand according to an embodiment of the present invention, and FIG. 8 is a view showing a whole control method of an apparatus for controlling an artificial hand according to an embodiment of the present invention. Here, the grip-type selection stage (S410) and the wrist-rotation selection stage (S420) may be reversed.

The apparatus for controlling the artificial hand according to an exemplary embodiment has effects as follows.

First, there is provided an apparatus for controlling an artificial hand, which is more convenient for an actual user who wants to control the artificial hand and has a more convenient algorithm.

Second, it is possible to solve a problem of signal degradation of an electromyogram caused by muscular fatigue or sweat due to long-time use.

Third, there is provided an apparatus for controlling an artificial hand, which can materializes a user's various commands.

Fourth, it is expected that disadvantaged disable persons can have better activities, thereby helping social participation and reducing socioeconomic costs.

Although a few exemplary embodiments of the present invention have been shown and described, it will be appreciated by those skilled in the art that changes may be made in these embodiments without departing from the principles and spirit of the invention, the scope of which is defined in the appended claims and their equivalents.

What is claimed is:

1. An apparatus to control a prosthetic hand, comprising:
   a display interface configured to be mounted on a head and to receive a signal of a movement of an eye;
   an electromyogram input configured to receive an electromyogram signal;
   a blink detector configured to detect a blink as a blink signal; and
   a controller configured to control movement of the prosthetic hand based on the signal of the movement of the eye, the electromyogram signal, and the blink signal,
   wherein the display interface comprises a camera configured track the movement of the eye,
   wherein the display interface further comprises a basic-mode, a gesture-mode, and a grip-mode,
   wherein the basic-mode is configured to enable selecting any one or any combination of any two or more of the gesture-mode, the grip mode, a command to bend an elbow of the prosthetic hand, and a command to stop operations of the prosthetic hand, and
   wherein the command to stop the operations of the prosthetic hand is selected, in response to the blink detector detecting a double blink.

2. The apparatus of claim 1, wherein the display interface is further configured to be worn on a face.

3. The apparatus of claim 2, wherein the display interface further comprises a pair of glasses or a pair of sunglasses.

4. The apparatus of claim 1, wherein the gesture-mode is configured to enable selecting any one or any combination of any two or more of a command to return to a previous stage, a command to return to the basic-mode, the command to bend the elbow of the prosthetic hand, the command to stop the operations of the prosthetic hand, a command to spread an index finger of the prosthetic hand while closing a pinky finger of the prosthetic hand, a ring finger of the prosthetic hand, a middle finger of the prosthetic hand, and a thumb of the prosthetic hand, and a command to spread a thumb of the prosthetic hand while closing the pinky finger of the prosthetic hand, the ring finger of the prosthetic hand, the middle finger of the prosthetic hand, and the index finger of the prosthetic hand.

5. The apparatus of claim 1, wherein the grip-mode enables a grip-type selection, a wrist-rotation selection, and an open/close selection.

6. The apparatus of claim 5, wherein the grip-type selection is configured enable selecting any one or any combination of any two or more of a command to return to a previous stage, a command to return to the basic-mode, the command to bend the elbow of the prosthetic hand, the command to stop the operations of the prosthetic hand, a command to the prosthetic hand to grip, a command to the prosthetic hand to grip while sticking out a thumb of the prosthetic hand, a command to the prosthetic hand to grip a circular object, a command to adjust fingers of the prosthetic hand to touch a small and circular object, and a command to enter a next stage.

7. The apparatus of claim 5, wherein the wrist-rotation selection is configured to enable selecting any one or any combination of any two or more of a command to return to a previous stage, a command to return to the basic-mode, the command to bend the elbow of the prosthetic hand, a command to stop operations of the prosthetic hand, a command to rotate a wrist of the prosthetic hand in a clockwise direction, a command to rotate the wrist of the prosthetic hand in a counterclockwise direction, and a command to enter a next stage.

8. The apparatus of claim 5, wherein the open/close selection is configured to enable selecting any one or any combination of any two or more of a command to return to a previous stage, a command to return to the basic-mode, the command to bend the elbow of the prosthetic hand, the command to stop the operations of the prosthetic hand, a command to open the prosthetic hand, and a command to close the prosthetic hand.

9. The apparatus of claim 1, wherein the controller is further configured to control the prosthetic hand based on a complementation of the signal of the movement of the eye and the electromyogram signal.

10. The apparatus of claim 1, wherein the controller is further configured to control the prosthetic hand based on a complementation of the signal of the movement of the eye and the blink signal.

11. An apparatus, comprising:
a prosthetic arm comprising an elbow, a thumb, an index finger, a middle finger, a ring finger, and a pinky finger;
an interface configured to be mounted on a head of a user and comprising a camera configured to track movement of an eye of the user, and a display configured to enable selection of a mode, among a basic mode, a gesture mode, and a grip mode, based on the movement of the eye;
an electromyograph configured to detect signals of the user to generate an electromyogram; and
a controller configured to control movement of the prosthetic arm based on the electromyogram and the selected mode,
wherein in response to being in the basic mode,
the display is further configured to
display an icon of the gesture mode, an icon of elbow bending, an icon of elbow extending, and either one of an icon of the grip mode and an icon of a wrist rotation mode,
transition to the gesture mode, in response to the icon of the gesture mode being selected by the movement of the eye, and
either transition to the grip mode, in response to the icon of the grip mode being selected by the movement of the eye, or transition to the wrist rotation mode, in response to the icon of the wrist rotation mode being selected by the movement of the eye, and
the controller is further configured to
bend the elbow based on the electromyogram, in response to the icon of elbow bending being selected by the movement of the eye, and
extend the elbow based on the electromyogram, in response to the icon of elbow extending being selected by the movement of the eye, and
wherein the controller is further configured to stop the operations of the prosthetic hand by detecting a double blink.

12. The apparatus of claim 11, wherein in response to being in the gesture mode,
the display is further configured to
display an icon of a previous mode, an icon of the basic mode, an icon of pointing, an icon of thumb-up, the icon of elbow bending, the icon of elbow extending, and an icon of stopping,
transition to a mode that is occupied immediately before being in the gesture mode, in response to the icon of the previous mode being selected by the movement of the eye, and
transition to the basic mode, in response to the icon of the basic mode being selected by the movement of the eye, and the controller is further configured to
extend the index finger and close the thumb, the middle finger, the ring finger, and the pinky finger, based on the electromyogram, in response to the icon of pointing being selected by the movement of the eye,
extend the thumb and close the index finger, the middle finger, the ring finger, and the pinky finger, based on the electromyogram, in response to the icon of thumb-up being selected by the movement of the eye,
bend the elbow based on the electromyogram, in response to the icon of elbow bending being selected by the movement of the eye, and
extend the elbow based on the electromyogram, in response to the icon of elbow extending being selected by the movement of the eye.

13. The apparatus of claim 11, wherein the display is further configured to display icons of grip types, in response to being in the grip mode, and constrain motion of the prosthetic arm to a grip type while the prosthetic arm is moving based on the electromyogram, in response to an icon of the grip type, among the icons of grip types, being selected by the movement of the eye.

14. The apparatus of claim 11, wherein the interface is further configured to be in one of the basic mode, the gesture mode, and the grip mode, at an exclusion of being in another two of the basic mode, the gesture mode, and the grip mode.

* * * * *